United States Patent [19]
Stevenson

[11] Patent Number: 5,261,353
[45] Date of Patent: Nov. 16, 1993

[54] UDDER CARE PLUS INDICATOR

[76] Inventor: Dale V. Stevenson, 940 Lake Shore Way, B-23, Lake Alfred, Fla. 33850

[21] Appl. No.: 863,254

[22] Filed: Apr. 3, 1992

Related U.S. Application Data

[63] Continuation-in-part of Ser. No. 608,918, Nov. 5, 1990, Pat. No. 5,101,770.

[51] Int. Cl.$^5$ ............................................. A01K 29/00
[52] U.S. Cl. .................................................... 119/157
[58] Field of Search ...................... 424/405; 119/14.01, 119/158, 159, 157

[56] References Cited

U.S. PATENT DOCUMENTS

| | | | |
|---|---|---|---|
| 4,113,857 | 9/1978 | Shetty | 424/78.25 |
| 4,554,305 | 11/1985 | Hall | 427/435 X |
| 4,761,247 | 8/1988 | Rei et al. | 424/405 X |
| 4,780,317 | 10/1988 | Sekikawa et al. | 424/405 X |
| 4,863,942 | 9/1989 | Wenk et al. | 514/381 |
| 5,101,770 | 4/1992 | Stevenson | 119/159 |

*Primary Examiner*—Gene Mancene
*Assistant Examiner*—Thomas Price
*Attorney, Agent, or Firm*—Charles A. McClure

[57] ABSTRACT

Post-milking udder care to assure udder disinfection, including coloring the udder with an iodine-free inorganic composition as an indicator of such treatment, including especially applying to the udder of a milking animal an aqueous solution of an alkali metal hypochlorite containing an alkali metal permanganate in such concentration as to be visible for at least a substantial period of time thereafter, if not up until the time of the next milking. Preferred compositions include several percent of sodium hypochlorite, with enough potassium permangananate to be visible for such a period of time on an udder to which it is applied.

20 Claims, No Drawings

UDDER CARE PLUS INDICATOR

This is a continuation-in-part of my copending patent application, Ser. No. 608,918, filed Nov. 5, 1990 (incorporated herein by this reference) and to issue as U.S. Pat. No. 5,101,770 on Apr. 7, 1992.

TECHNICAL FIELD

This invention relates to udder care of domestic animals milked for human benefit, including means and methods of disinfecting the udder, including the teats, to safeguard against infection, plus visible indication that disinfectant has been applied after milking.

BACKGROUND OF THE INVENTION

Sanitation in food preparation is usually principally for the direct benefit of the consumer, but where the food is produced by a living animal, as in the instance of milk, it is also desirable to safeguard the animal—as well as the product—by taking suitable sanitary precautions. The udder and particularly the teats of milk animals are highly susceptible to infection from contact with flies, manure, people's hands, etc. Hence, good milking technique includes assured application of suitable disinfecting composition.

For many years the preferred germicide in disinfectants for such use has been iodine, which in elemental form is not soluble in water (though some of its salts and other combined forms are) but is soluble in alcohol and many other organic liquids. Its traditional popularity stems in part from the characteristically intransigent stain it leaves as visible evidence of its application. However, it and its customary liquid formulations foster chapping and cracking, which not only are painful but also provide new sites for infection.

Iodophoric compositions advanced as less troublesome are found in these representative U.S. Pat. Nos.: Hall 3,663,694 (ethoxylated lanolin), Eckols 4,012,504 (mineral oil, with polyoxyethylene cetyl ether), Foll et al. 4,288,428 (alkylphenoxypoly[ethyleneoxy]ethanol or polyvinylpyrrolidone), Lauermann et al. 4,466,959 (glycerin, paraffin oil, and higher fatty acids), and Witkin (povidone-iodine complex plus hydrogen peroxide). Such efforts suggest that there is a need for further improvements in this art, preferably a new departure rather than simply more—or more varied—iodophors.

Other germicides have been made the basis of disinfectants for udder treatment. The efficacy of chlorine-containing compositions, specifically hypochlorites ("Clorox") is reported in *Journal of Dairy Science*, vol. 56, no. 1, p. 148 (Jan. 1973) and references cited therein. However, though efficacious, they have not been generally accepted, in part because of tradition, and in part for lack of coloring or equivalent identifiability so as to enable positive monitoring that the treatment has actually been accomplished.

Lasting colorizers of hypochlorite bleaches used for different purposes also are identified in such U.S. Pat. Nos. as Kitchen et al. 3,544,373 (phthalocyanines), Hung 4,536,367 (triphenylmethanes), and Sudbury 4,457,855 (anthraquinones), for example. However, they are not suitable for the present purpose because of their persistence.

Prince U.S. Pat. No. 3,950,554, while urging the use of a fatty acid ester plus drying oil to form a water-resistant film on udders, included a suggestion of an edible organic dye, such as carotene, as well as hypochlorites, iodophors, and/or other udder disinfectants. His teachings failed to make any appreciable impression on the art, at least in the direction suggested above as being desirable here.

My aforementioned contribution to this art provided a two-step post-milking and pre-milking method of udder care, including steps of applying an iodine-free colorizing liquid thereto after milking, then decolorizing the udder by another liquid application before the next milking. Such practice is still effective and appropriate, but it may be modified and simplified under appropriate circumstances.

SUMMARY OF THE INVENTION

A primary object of the present invention is to include visible coloration with udder disinfectant application to milk animals, preferably promptly after milking, as an indicator of disinfection.

Another object of this invention is provide an option of udder coloration lasting until the next milking, for pre-milking removal by a decolorant, or alternatively not so long-lasting--so that no separate pre-milking udder treatment is required for decolorizing.

A further object of the invention is to eliminate or ameliorate undesired side-effects by using non-iodophoric disinfectants.

In general, the objects of the present invention are attained, in a method of udder care, by coloring such udder in a post-milking disinfecting step—free of iodine, organic dyes, etc. The coloring informs all who see an animal with udder so marked that appropriate post-milking disinfection of it has been accomplished. Moreover, this invention gives a dairy farmer or manager also the option to determine whether it is preferable to have the coloring endure until the next milking, for removal by a pre-milking decolorizing step, or whether a shorter duration is preferable. If exposure to ambient conditions for only part of the time intervening between one milking and the next suffices to decolorize an udder so colored, a pre-milking decolorizing step is not needed to legitimize coloring as an indicator of disinfection at the forthcoming milking. If a separate pre-milking application is preferred as more conclusive or for other reason(s), longer-lasting post-milking colorizing, plus pre-milking decolorizing, as disclosed in my noted patent, is readily available.

According to this invention, at post-milking a coloring and disinfecting step is performed, by applying to the udder aqueous anti-microbial solution colored with a permanganate at a concentration sufficient to be visible at that time and for at least a substantial part of the time intervening until the next milking. The solution may be suitably low in permanganate concentration so the resulting coloration of the udder fades under ambient conditions by the next milking, thus rendering a pre-milking decolorizing step avoidable.

Other objects of the present invention, together with means and methods for attaining the various objects, will be apparent from the following description of preferred embodiments, which are presented by way of example rather than limitation.

DESCRIPTION OF THE INVENTION

By this invention, a milking animal's udder, normally bathed in an antimicrobial solution promptly after milking, is also colorized in the same disinfecting step by inclusion of a suitable iodine-free inorganic colorizing composition. The animal's colored udder serves as a visible indicator that a proper disinfecting step has actually been performed—rather than accidentally or intentionally neglected.

The resulting color should persist on an udder so treated for at least a substantial part of the time intervening from one milking to the next, such as the time required to milk an entire herd. The intensity of applied color may be so controlled that under ambient conditions it either endures to the time of the next milking or not, depending upon whether separate pre-milking bathing of the udder is deemed desirable. Obviously, if the color is gone by the time of the next milking, a separate pre-milking decolorizing step may be omitted. If not, a decolorizing solution is applied to the udder before milking, as disclosed in my noted patent. The dairy farmer or manager can adjust the colorizing intensity so as to require a separate pre-milking decolorizing step or not, whichever is desired.

The preferred post-milking udder-coloring and disinfecting composition of this invention is an aqueous antimicrobial solution with an effective concentration (at least a trace) of permanganate for coloring. All erstwhile students of chemistry know the persistent purplish brown stain of permanganate, but heretofore it has not been utilized as in this invention. Preferred as the anti-microbial or disinfectant composition is hypochlorite solution (a few percent).

Both these ingredients are suitably alkali metal compositions, such as sodium hypochlorite and potassium permanganate. Emollients, such as lanolin, may be added to ameliorate effects of milking and of frequent application of disinfecting liquid to the udder. This procedure can be accomplished manually by conventional teat dip cup and sponge, or by semi-automated spraying or similar procedure. No illustration of such conventional procedures is necessary here, as they are well known to persons skilled in caring for dairy animals.

A permanganate-stained udder indicates at a glance that it was treated with disinfectant. If the treated animal engages in normal outside exposure to air, grass, and sun, the preferred concentration of permanganate may be selected higher than when confined to a barn or other covered area. Alternatively, an intermediate concentration could be used for both, whereupon the degree of coloration remaining at the next milking might also be interpreted as an indicator of the animal's activity and the ambient conditions to which it was exposed during the time period intervening between one milking and the next.

As an example, permanganate granules can be suspended within a porous membrane in a given volume of water for a given period of time or to a desired degree of coloration, with or without stirring. With moderate circulation, an hour should suffice for an ounce of potassium permanganate in a gallon of water. The water, which takes on a permanganate color, is decanted off into an appropriate aqueous hypochlorite solution of known volume. The color is conveniently controllable by adjusting either the permanganate perfusion time or the ratio of dilution (or both). With the suggested time, moderate dilution such as nine or ten times the volume of the colored water suffices for an intermediate duration of udder coloration. To be assured of color persistence to the next milking, at most half such ratio is preferable. To assure that a decolorizing step will be superfluous, at least about twice such dilution ratio is recommended. Solution color can be checked either by eye or by colorimeter, but better is the udder coloration from a particular formulation method.

Sodium hypochlorite at low single-digit percentages have the desired antimicrobial action and a low enough pH (at most 9 to 10) to limit caustic irritation. The concentration range from at least about 2 to at most about 5 (preferably several) percent is suitable. Double-digit percentages are harmful as too caustic (pH 11 to 12).

If, at the next milking, the residual coloration of the udder is such that someone might conclude wrongly after the milking that the post-milking disinfecting step had just been performed, a pre-milking decolorizing step is highly recommended. As disclosed in my mentioned patent such step may be performed by dipping, spraying, or sponging the udder appropriately. A preferred decolorizing liquid comprises an acidic aqueous peroxide solution, having a few volume percent of hydrogen peroxide and of acetic acid, respectively.

Advantages and benefits of the composition and the method of this invention have been noted here and are readily recognizable. Others doubtless will accrue to persons who practice the invention, as well as to the animals upon which they practice it. Preferred embodiments and variants of the invention have been described here. Other modifications may be made, as by adding, combining, deleting, or subdividing compositions, parts, or steps, while retaining all or some of the advantages and benefits of the present invention—which itself is defined in the following claims.

I claim:

1. An iodine-free aqueous antimicrobial composition adapted to disinfect an udder of a milk animal including an iodine-free inorganic material adapted upon application to the udder to color it for at least a substantial part of the time intervening between successive milkings.

2. The composition of claim 1 with a pH at most about 9 to 10.

3. The composition of claim 1 wherein the inorganic coloring material comprises a permanganate.

4. The composition of claim 1 comprising a several percent hypochlorite solution as the antimicrobial disinfectant.

5. The composition of claim 1 comprising an aqueous solution of about 2 to 5 percent sodium hypochlorite and sufficient potassium permanganate to color the udder of a milk animal to which applied.

6. Alkaline solution comprising an iodine-free antimicrobial composition effective to disinfect the udder of a milk animal upon application thereto after milking, and an iodine-free inorganic coloring agent effective to color the udder as an indicator of such disinfection for at least a substantial part of the time intervening from such application to the next milking of the same animal.

7. The composition of claim 6, effective to color the udder for a period of time extending to the next milking of the animal.

8. The composition of claim 6, effective to color the udder for a period of time not extending to the next milking of the animal.

9. The composition of claim 6 having a pH of at most 10 to 11.

10. Method of udder care with indication thereof, comprising applying to the udder of a milking animal an aqueous solution of an iodine-free disinfectant including an inorganic coloring agent adapted to color the udder upon application thereto as an indicator thereof.

11. Method of udder care according to claim 10, wherein the aqueous solution is applied to the udder promptly after milking it.

12. Method of udder care according to claim 10, including sufficient coloring agent to color the udder for at least a substantial part of the period of time intervening before the next milking.

13. Method of udder care according to claim 12, including insufficient coloring agent is used to color the udder for the entire period of time intervening before the next milking.

14. Method of udder care according to claim 10, wherein the iodine-free disinfectant comprises an alkali metal hypochlorite, and the inorganic coloring agent comprises an alkali metal permanganate.

15. Milk-animal udder-coloring disinfectant-indicating aqueous composition, comprising hypochlorite as a disinfectant and potassium permanganate as the principal coloring agent.

16. Milk-animal udder-coloring disinfectant-indicating composition according to claim 15, wherein potassium permanganate is the sole coloring agent therein.

17. Milk-animal udder-coloring disinfectant-indicating composition according to claim 15, applied topically to the udder of a milk animal.

18. Composition according to claim 17, applied thereto at a given milking, and decolorizable at the next milking.

19. Composition according to claim 18, decolorizable upon application of a hydrogen peroxide solution to the same udder.

20. Composition applied to an udder according to claim 17, decolorizable by passage of time before the next milking.

* * * * *